US010941371B2

(12) United States Patent
Herbst et al.

(10) Patent No.: US 10,941,371 B2
(45) Date of Patent: Mar. 9, 2021

(54) *BACILLUS GIBSONII* PROTEASE AND VARIANTS THEREOF

(71) Applicant: Henkel AG & Co. KGaA, Duesseldorf (DE)

(72) Inventors: Daniela Herbst, Duesseldorf (DE); Timothy O'Connell, Landsberg am Lech (DE); Nina Mussmann, Willich (DE); Inga Kerstin Vockenroth, Duesseldorf (DE); Thomas Weber, Marburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/309,236

(22) PCT Filed: Jun. 1, 2017

(86) PCT No.: PCT/EP2017/063253
§ 371 (c)(1),
(2) Date: Dec. 12, 2018

(87) PCT Pub. No.: WO2017/215925
PCT Pub. Date: Dec. 21, 2017

(65) Prior Publication Data
US 2019/0144792 A1 May 16, 2019

(30) Foreign Application Priority Data
Jun. 15, 2016 (DE) .................... 10 2016 210 628.7

(51) Int. Cl.
*C11D 3/386* (2006.01)
*C12N 9/54* (2006.01)
*C12N 9/50* (2006.01)

(52) U.S. Cl.
CPC .............. *C11D 3/386* (2013.01); *C12N 9/50* (2013.01); *C12N 9/54* (2013.01); *C12Y 304/21062* (2013.01)

(58) Field of Classification Search
CPC .......................... C11D 3/386; C12Y 304/21062
USPC ........................................................ 435/212
See application file for complete search history.

(56) References Cited

U.S. PATENT DOCUMENTS

| 5,336,611 | A | 8/1994 | van Eekelen et al. |
| 7,449,187 | B2 | 11/2008 | Weber et al. |
| 8,785,171 | B2 | 7/2014 | Souter et al. |
| 9,260,706 | B2 | 2/2016 | Wieland et al. |
| 9,528,100 | B2 | 12/2016 | Fano et al. |
| 2016/0319266 | A1 | 11/2016 | Kolkman et al. |

FOREIGN PATENT DOCUMENTS

| EP | 0328229 A1 | 6/1989 |
| WO | 03006602 A2 | 1/2003 |
| WO | 03054185 A1 | 7/2003 |
| WO | 2011072117 A1 | 6/2011 |
| WO | 2012119955 A1 | 9/2012 |
| WO | 2015089447 A1 | 6/2015 |

OTHER PUBLICATIONS

USPTO in house Blast SID1 of Wieland et al, 2012 (WO2012/119955). Alignment with SID1 herein.*
Guo et al, Protein tolerance to random amino acid change. Proc Natl Acad Sci U S A. Jun. 22, 2004;101(25):9205-9210. Epub Jun. 14, 2004.*
Acc#A0A061NWP5 Kudo et al, "Draft Genome Sequences of *Geomicrobium* sp. Strains JCM 19037, JCM 19038, JCM 19039, and JCM 19055, Isolated from Aquatic Samples.", Genome Announc. 2:e00622-14(2014). Alignment with SID5.*
Henkel et al, Novel Alkaline Protease from Bacillus Gibsonii and Washing and Cleaning Agents Containing Said Novel Alkaline Protease SID3 from US20090275493A1. Alignment with SID5.*
EPO, International Search Report issued in International Application No. PCT/EP2017/063253 dated Aug. 14, 2017.

* cited by examiner

*Primary Examiner* — Sheridan Swope
(74) *Attorney, Agent, or Firm* — Lorenz & Kopf, LLP

(57) ABSTRACT

The present disclosure relates to proteases that are variants of a *Bacillus gibsonii* protease, the proteases comprising an amino acid sequence which has at least about 70% sequence identity to the amino acid sequence given in SEQ ID No. 1 over its entire length, and which has an amino acid substitution on at least one of the positions corresponding to the positions 12, 43, 122, 127, 154, 156, 160, 211 or 222, relating in each case to the numbering according to SEQ ID No. 1. The present disclosure also relates to the production and use thereof. Said type of proteases have a very good cleaning performance.

14 Claims, No Drawings
Specification includes a Sequence Listing.

SEQUENCE LISTING

```
<160> NUMBER OF SEQ ID NOS: 9

<210> SEQ ID NO 1
<211> LENGTH: 269
<212> TYPE: PRT
<213> ORGANISM: Bacillus gibsonii

<400> SEQUENCE: 1

Gln Gln Thr Val Pro Trp Gly Ile Thr Arg Val Gln Ala Pro Thr Val
1               5                   10                  15
```

```
His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 2
<211> LENGTH: 269
<212> TYPE: PRT
<213> ORGANISM: Artificial Sequence
<220> FEATURE:
<223> OTHER INFORMATION: Protease Variante

<400> SEQUENCE: 2

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Val Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110
```

```
Ala Thr Asn Asn Met His Ile Ala Asn Met Ser Leu Gly Ser Asp Ala
            115                 120                 125

Pro Ser Thr Thr Leu Glu Arg Ala Val Asn Tyr Ala Thr Ser Arg Gly
        130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265
```

<210> SEQ ID NO 3
<211> LENGTH: 269
<212> TYPE: PRT
<213> ORGANISM: Artificial Sequence
<220> FEATURE:
<223> OTHER INFORMATION: Protease Variante

<400> SEQUENCE: 3

```
Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Leu Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Ser Gly Ala Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205
```

```
Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 4
<211> LENGTH: 269
<212> TYPE: PRT
<213> ORGANISM: Artificial Sequence
<220> FEATURE:
<223> OTHER INFORMATION: Protease Variante

<400> SEQUENCE: 4

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
                100                 105                 110

Ala Thr Asn Asn Met His Ile Ala Asn Met Ser Leu Gly Ser Asp Ala
            115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
                180                 185                 190

Val Ala Pro Gly Val Gly Ile Gln Ser Thr Tyr Leu Asn Asn Ser Tyr
            195                 200                 205

Ala Ser Asn Asp Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 5
<211> LENGTH: 269
<212> TYPE: PRT
<213> ORGANISM: Artificial Sequence
<220> FEATURE:
```

<223> OTHER INFORMATION: Protease Variante

<400> SEQUENCE: 5

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Leu Asp Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 6
<211> LENGTH: 269
<212> TYPE: PRT
<213> ORGANISM: Artificial Sequence
<220> FEATURE:
<223> OTHER INFORMATION: Protease Variante

<400> SEQUENCE: 6

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

```
Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Ser
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 7
<211> LENGTH: 269
<212> TYPE: PRT
<213> ORGANISM: Artificial Sequence
<220> FEATURE:
<223> OTHER INFORMATION: Protease Variante

<400> SEQUENCE: 7

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Pro Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Leu Asp Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Asp Ala Ala Thr Arg
            260                 265

<210> SEQ ID NO 8
<211> LENGTH: 269
<212> TYPE: PRT
<213> ORGANISM: Artificial Sequence
<220> FEATURE:
<223> OTHER INFORMATION: Protease Variante

<400> SEQUENCE: 8

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met His Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Asp Ala Ala Thr Arg
            260                 265
```

```
<210> SEQ ID NO 9
<211> LENGTH: 269
<212> TYPE: PRT
<213> ORGANISM: Artificial Sequence
<220> FEATURE:
<223> OTHER INFORMATION: Protease Variante

<400> SEQUENCE: 9

Gln Gln Thr Val Pro Trp Gly Ile Thr Arg Val Leu Ala Pro Thr Val
1               5                   10                  15

His Asn Arg Gly Ile Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
        50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
                100                 105                 110

Ala Thr Asn Asn Met His Ile Ala Asn Leu Ser Leu Gly Ser Asp Ala
            115                 120                 125

Pro Ser Thr Thr Leu Glu Arg Ala Val Asn Tyr Ala Thr Ser Arg Gly
        130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
                180                 185                 190

Val Ala Pro Gly Val Gly Ile Gln Ser Thr Tyr Leu Asn Asn Ser Tyr
            195                 200                 205

Ala Ser Met Pro Gly Thr Ser Met Ala Thr Pro His Val Ser Gly Val
        210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265
```

BACILLUS GIBSONII PROTEASE AND VARIANTS THEREOF

CROSS-REFERENCE TO RELATED APPLICATION

This application is a U.S. National-Stage entry under 35 U.S.C. § 371 based on International Application No PCT/EP2017/063253, filed Jun. 1, 2017 which was published under PCT Article 21(2) and which claims priority to Application No. 10 2016 210 628.7, filed Jun. 15, 2016, which are all hereby incorporated in their entirety by reference.

TECHNICAL FIELD

The present disclosure lies in the field of enzyme technology. The present disclosure relates to proteases from *Bacillus gibsonii*, the amino acid sequence of which was modified, in particular with a view to use in washing agents and cleaning agents, in order to give said proteases better cleaning performance in the removal of protein-containing stains, in particular with respect to dried-up or burned-in stains, and to the nucleic acids coding for said proteases and the production of said proteases. The present disclosure also relates to the uses of said proteases, methods in which said proteases are used, and agents containing said proteases, in particular washing agents and cleaning agents.

BACKGROUND

Proteases are among the enzymes of greatest technical importance. For washing agents and cleaning agents, proteases are the longest established enzymes and are contained in practically all modern, high-performance washing agents and cleaning agents. Proteases cause the breakdown of protein-containing stains on the goods to be cleaned. Among proteases, in turn, subtilisin-type proteases (subtilases, subtilopeptidases, EC 3.4.21.62) are especially important, which are serine proteases because of the catalytically active amino acids. Subtilisin-type proteases act as non-specific endopeptidases and hydrolyze any acid-amide bonds located in the interior of peptides or proteins. The pH optimum of subtilisin-type proteases is usually in the clearly alkaline range. An overview of this family is provided, for example, by the article "Subtilases: Subtilisin-like Proteases" by R. Siezen, pages 75-95 in "Subtilisin enzymes," published by R. Bott and C. Betzel, New York, 1996. Of course, subtilases are formed by microorganisms; among them, in particular the subtilisins formed and secreted by *Bacillus* species should be mentioned as the most important group within the subtilases.

Examples of the subtilisin-type proteases preferably used in washing agents and cleaning agents are the subtilisins BPN' and Carlsberg, protease PB92, subtilisins 147 and 309, the protease from *Bacillus lentus*, in particular from *Bacillus lentus* DSM 5483, subtilisin DY, and the enzymes thermitase, proteinase K, and proteases TW3 and TW7, which should be classed as subtilases but no longer as subtilisins in the narrower sense, and variants of the mentioned proteases having an amino acid sequence that is modified in comparison with the initial protease. Proteases are modified in a specific manner or randomly by methods known from the prior art and thus, for example, optimized for use in washing agents and cleaning agents. This includes point, deletion, or insertional mutagenesis or fusion with other proteins or protein parts. Thus, appropriately optimized variants are known for most proteases known from the prior art.

In general, only selected proteases are suitable for use in liquid surfactant-containing preparations. Many proteases do not exhibit sufficient catalytic performance in such preparations. Therefore, for the use of proteases in cleaning agents, high catalytic activity under conditions existing during a washing process is especially desirable.

Surprisingly, it has now been found that a protease from *Bacillus gibsonii* or a protease sufficiently similar thereto (with respect to sequence identity) having an amino acid substitution in at least one of the positions that correspond to positions 12, 43, 122, 127, 154, 156, 160, 211, 212, and 222, in each case with respect to the numbering according to SEQ ID NO:1, is improved with respect to the proteolytic activity under standard washing conditions in comparison with the wild-type form and therefore is especially suitable for use in washing or cleaning agents.

Therefore, in a first aspect, the present disclosure relates to a protease comprising an amino acid sequence that has at least about 70% sequence identity to the amino acid sequence specified in SEQ ID NO:1 over the entire length thereof and that has an amino acid substitution in at least one of the positions that correspond to positions 12, 43, 122, 127, 154, 156, 160, 211, 212, and 222, in each case with respect to the numbering according to SEQ ID NO:1.

The present disclosure also relates to a method for producing a protease, comprising substituting an amino acid in at least one position that corresponds to positions 12, 43, 122, 127, 154, 156, 160, 211, 212, or 222 in SEQ ID NO:1, in an starting protease that has at least 70% sequence identity to the amino acid sequence specified in SEQ ID NO:1 over the entire length thereof, preferably in such a way that the protease has at least one of the amino acid substitutions Q12L, I43V, M122L, D127P, N154S, T156A, G160S, M211N, M211L, P212D, P212H, or A222S.

Therefore, a protease in the sense of the present patent application comprises both the protease as such and a protease produced by employing a method as contemplated herein. All statements with respect to the protease therefore relate both to the protease as such and to the proteases produced by employing corresponding methods.

Further aspects of the present disclosure relate to the nucleic acids that code for said proteases, non-human host cells containing proteases or nucleic acids as contemplated herein, and agents comprising proteases as contemplated herein, in particular washing agents and cleaning agents, washing methods and cleaning methods, and uses of the proteases as contemplated herein in washing or cleaning agents to remove protein-containing stains.

"At least one," as used herein, means one or more, i.e. about 1, about 2, about 3, about 4, about 5, about 6, about 7, about 8, about 9, about 10, about 11, about 12, about 13, about 14, or more.

BRIEF SUMMARY

A protease is provided herein. The protease includes an amino acid sequence that has at least about 70% sequence identity to the amino acid sequence specified in SEQ ID NO:1 over the entire length thereof and that has an amino acid substitution in at least one of the positions that correspond to positions Q12, I43, M122, D127, N154, T156, G160, M211, P212, or A222, in each case with respect to the numbering according to SEQ ID NO:1.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure is based on the surprising discovery of the inventors that an amino acid substitution in at least one of the positions that correspond to positions 12, 43, 122, 127, 154, 156, 160, 211, 212, or 222 of the protease from *Bacillus gibsonii* according to SEQ ID NO:1, in a protease that comprises an amino acid sequence having at least about 70% identity to the amino acid sequence specified in SEQ ID NO:1, such that the amino acids 12L, 43V, 122L, 127P, 154S, 156A, 160S, 211N, 211L, 212D, 212H, or 222S are present in at least one of the corresponding positions, causes improved catalytic activity of this altered protease in washing agents and cleaning agents. This is surprising in particular because none of the amino acid substitutions mentioned above was previously linked to increased catalytic activity of the protease. In various embodiments, the starting amino acids in the positions mentioned above, i.e. the amino acids to be substituted, are Q12, I43, M122, D127, N154, T156, G160, M211, M211, P212, P212, and/or A222.

The proteases as contemplated herein have increased catalytic activity in washing or cleaning agents. In various embodiments, the proteases as contemplated herein have a proteolytic activity that is at least about 110%, at about least 115%, at least about 120%, at least about 125%, at least about 130%, at least about 135%, at least about 140%, at least about 145%, at least about 150%, at least about 155%, or at least about 160% in relation to the wild-type variant of the protease (SEQ ID NO:1). Such proteases having improved performance enable improved washing results on proteolytically sensitive stains in various temperature ranges, in particular in a temperature range of from about 40° C. to about 60° C.

The proteases as contemplated herein have enzymatic activity, i.e. said proteases are capable of hydrolyzing peptides and proteins, in particular in a washing or cleaning agent. A protease as contemplated herein is therefore an enzyme which catalyzes the hydrolysis of amide/peptide bonds in protein/peptide substrates and which is therefore capable of cleaving proteins or peptides. Furthermore, a protease as contemplated herein is preferably a mature protease, i.e. the catalytically active molecule without signal peptide(s) and/or pro-peptide(s). Unless otherwise specified, the specified sequences also relate to mature (processed) enzymes.

In various embodiments of the present disclosure, the protease is a free enzyme. This means that the protease can directly act with all components of an agent and, if the agent is a liquid agent, that the protease is in direct contact with the solvent of the agent (e.g. water). In other embodiments, an agent can contain proteases that form an interaction complex with other molecules or that contain a "casing." In this case, a single protease molecule or a plurality of protease molecules can be separated from the other components of the agent by a structure surrounding said protease molecule or molecules. Such a separating structure can arise by employing vesicles, such as a micelle or a liposome, but is not limited thereto. The surrounding structure can also be a virus particle, a bacterial cell, or a eukaryotic cell. In various embodiments, an agent can contain cells of *Bacillus gibsonii* or *Bacillus subtilis* that express the proteases as contemplated herein or cell culture supernatants of such cells.

Furthermore, in various embodiments the protease as contemplated herein contains at least one amino acid substitution selected from the group including of Q12L, I43V, M122L, D127P, N154S, T156A, G160S, M211N, M211L, P212D, P212H, or A222S, in each case with respect to the numbering according to SEQ ID NO:1. In a further preferred embodiment, the protease as contemplated herein contains one of the following amino acid substitution variants: (I) I43V; (II) M122L, N154S, and T156A; (III) M211N and P212D; (IV) M211L and P212D; (V) G160S; (VI) D127P, M211L, and P212D; (VII) P212H; or (VIII) Q12L, M122L, and A222S, the numbering relating to the numbering according to SEQ ID NO:1 in each case.

In another embodiment of the present disclosure, the protease comprises an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, and about 98.8% identical to the amino acid sequence specified in SEQ ID NO:1 over the entire length thereof and that has one or more of the amino acid substitutions 12L, 43V, 122L, 127P, 154S, 156A, 160S, 211N, 211L, 212D, 212H, or 222S in at least one of the positions that correspond to positions 12, 43, 122, 127, 154, 156, 160, 211, 212, or 222 in the numbering according to SEQ ID NO:1. In the context of the present disclosure, the feature that a protease has the indicated substitutions means that the protease contains at least one of the corresponding amino acids in the corresponding positions, i.e. not all of the 10 positions are otherwise mutated or, e.g. as a result of fragmentation of the protease, deleted. The amino acid sequences of such proteases that are preferred as contemplated herein are specified in SEQ ID Nos: 2-9.

The identity of nucleic acid sequences or amino acid sequences is determined by employing a sequence comparison. This sequence comparison is based on the commonly used BLAST algorithm established in the prior art (see, for example, Altschul, S. F., Gish, W., Miller, W., Myers, E. W., & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pp. 3389-3402) and is performed basically by associating similar sequences of nucleotides or amino acids in the nucleic acid sequences or amino acid sequences with each other. A tabular association of the positions in question is referred to as an alignment. A further algorithm available in the prior art is the FASTA algorithm. Sequence comparisons (alignments), in particular multiple sequence comparisons, are created by employing computer programs. For example, the Clustal series (see, for example, Chenna et al. (2003): Multiple sequence alignment with the Clustal series of programs. Nucleic Acid Research 31, 3497-3500), T-Coffee (see, for example, Notredame et al. (2000): T-Coffee: A novel method for multiple sequence alignments. J. Mol. Biol. 302, 205-217), or programs based on these programs or algorithms are frequently used. Also possible are sequence comparisons (alignments) by employing the computer program Vector NTI® Suite 10.3 (Invitrogen Corporation, 1600 Faraday Avenue, Carlsbad, Calif., USA) with the specified standard parameters, the AlignX module of which computer program for the sequence comparisons is based on ClustalW. Unless otherwise stated, the sequence identity specified herein is determined by employing the BLAST algorithm.

Such a comparison also enables a statement about the similarity of the compared sequences to each other. This similarity is commonly stated in percent identity, i.e. the percentage of identical nucleotides or amino acid residues in the same positions or in positions corresponding to each other in an alignment. The broader concept of homology also takes into consideration conservative amino acid exchanges in the case of amino acid sequences, i.e. amino acids having similar chemical activity, because they usually have similar chemical activity within the protein. Therefore, the similarity of the compared sequences can also be stated as percent homology or percent similarity. Identity and/or homology statements can be made over whole polypeptides or genes or only over individual ranges. Homologs or identical ranges of different nucleic acid sequences or amino acid sequences are therefore defined by homologies in the sequences. Such ranges often have identical functions. They can be small or comprise only a few nucleotides or amino acids. Such small ranges often have functions that are essential to the overall activity of the protein. Therefore, it can be sensible to relate sequence homologies only to individual, possibly small ranges. However, unless otherwise indicated, identity or homology statements in the present application relate to the entire length of the indicated nucleic acid sequence or amino acid sequence.

In the context of the present disclosure, the specification that an amino acid position corresponds to a numbered position in SEQ ID NO:1 therefore means that the corresponding position is associated with the numbered position in SEQ ID NO:1 in an alignment as defined above.

In a further embodiment of the present disclosure, the protease is exemplified in that the cleaning performance thereof is not significantly reduced in comparison with the cleaning performance of a protease that comprises an amino acid sequence that corresponds to the amino acid sequence specified in SEQ ID NO:1, i.e. the protease has at least about 80% of the reference washing performance, preferably at least about 100%, more preferably at least about 110% or more. The cleaning performance can be determined in a washing system that contains an automatic dishwashing agent in a dosage as specified herein and the protease, the proteases to be compared being used in equal concentrations (in relation to active protein) and the cleaning performance with respect to a stain of tea, meat, spaghetti, and/or crème bûlée being determined by measuring the degree of cleaning of the washed dishes. For example, the washing process can occur for about 57 minutes at a temperature of about 44° C. and the water can have a water hardness of between from about 5 and about 25°, preferably from about 10 and about 22°, more preferably from about 18 and about 22°, and even more preferably from about 20.5 and about 21.5° (German hardness). The concentration of the protease in the cleaning agent intended for this washing system is from about 0.001 to about 0.1 wt. %, preferably from about 0.01 to about 0.06 wt. %, in relation to active, cleaned protein.

A liquid reference agent for such a washing system can be composed as specified in table 2.

In the context of the present disclosure, the cleaning performance is determined, for example, at 45° C. using a dishwashing agent as indicated above, the washing process occurring preferably for 57 minutes with a holding time of 8 minutes.

By using the proteases in such a way that activity is equal, it is ensured that, even in the event of any divergence of the ratio of active substance to total protein (the values of the specific activity), the enzymatic properties, e.g. the cleaning performance on certain stains, are compared. In general, a low specific activity can be compensated by adding a greater amount of protein. Furthermore, the enzymes to be examined can also be used in an equal amount of substance or amount by weight if the enzymes to be examined have a different affinity for the test substrate in an activity test. In this context, the expression "equal amount of substance" refers to the use of the enzymes to be examined in equal molar quantities. The expression "equal amount by weight" refers to the use of the enzymes to be examined in equal amounts by weight.

Otherwise, methods for determining the protease activity are familiar to a person skilled in the field of enzyme technology and are routinely applied by said person skilled in the art. For example, such methods are disclosed in "Tenside," volume 7 (1970), pp. 125-132. Alternatively, the protease activity can be determined by employing the release of the chromophore para-nitroaniline (pNA) from the substrate suc-L-Ala-L-Ala-L-Pro-L-Phe-p-Nitroanilide (AAPF). The protease cleaves the substrate and releases pNA. The release of the pNA causes an increase in the extinction at 410 nm, the time curve of which is a measure of the enzymatic activity (see Del Mar et al., 1979). The measurement occurs at a temperature of about 25° C., a pH of about 8.6, and a wavelength of about 410 nm. The measurement time is about 5 min and the measurement interval is from about 20 s to about 60 s. The protease activity is typically specified in protease units (PE). Suitable protease activities are, for example, 2.25, 5, or 10 PE per ml of dishwashing liquor or dishwashing process. However, the protease activity is not equal to zero.

An alternative test for determining the proteolytic activity of the proteases as contemplated herein is an optical measurement method, preferably a photometric method. The test suitable for this purpose comprises the protease-dependent cleaving of the substrate protein casein. Casein is cleaved by the protease into a multitude of smaller partial products. The entirety of said partial products has increased absorption at about 290 nm in comparison with uncleaved casein. This increased absorption can be determined by employing a photometer and thus a conclusion can be drawn regarding the enzymatic activity of the protease.

The protein concentration can be determined by employing known methods, such as the BCA method (bicinchoninic acid; 2,2'-biquinolyl-4,4'-dicarboxylic acid) or the Biuret method (A. G. Gornall, C. S. Bardawill, and M. M. David, J. Biol. Chem., 177 (1948), pp. 751-766). In this regard, the active protein concentration can be determined by employing a titration of the active centers by employing a suitable irreversible inhibitor and determination of the residual activity (see M. Bender et al., J. Am. Chem. Soc. 88, 24 (1966), pp. 5890-5913).

In addition to the amino acid modifications explained above, proteases as contemplated herein can have further amino acid modifications, in particular amino acid substitutions, insertions, or deletions. Such proteases are further developed, for example, by specific genetic modification, i.e. by mutagenesis methods, and are optimized for certain intended uses or with respect to specific properties (e.g. with respect to their catalytic activity, stability, etc.). Furthermore, nucleic acids as contemplated herein can be introduced into recombination formulations and thus can be used to produce proteases or other polypeptides of completely new types.

The goal is to introduce specific mutations such as substitutions, insertions, or deletions into the known molecules in order, for example, to improve the cleaning performance of enzymes as contemplated herein. For this purpose, in particular the surface charges and/or the isoelectric point of the molecules can be changed and thereby the interactions of the molecules with the substrate can be changed. For example, the net charge of the enzymes can be changed in order to thereby influence the substrate binding, in particular for use in washing agents and cleaning agents. Alternatively or in addition, the stability or catalytic activity of the protease can be increased by employing one or more appropriate mutations and thereby the cleaning performance of the protease can be improved. Advantageous properties of individual mutations, e.g. individual substitutions, can complement each other. A protease already optimized with respect to certain properties, e.g. with respect to the stability of the protease during storage, can therefore be additionally further developed in the context of the present disclosure.

The following convention is used to describe substitutions that concern exactly one amino acid position (amino acid exchanges): first the naturally present amino acid is indicated in the form of the internationally customary single-letter code, followed by the associated sequence position and finally the introduced amino acid. Several exchanges within the same polypeptide chain are separated from each other by forward slashes. In the case of insertions, additional amino acids are named after the sequence position. In the case of deletions, the missing amino acid is replaced by a symbol, such as an asterisk or a dash, or an A is specified before the corresponding position. For example, P14H describes the substitution of proline in position 14 for histidine, P14HT describes the insertion of threonine after the amino acid histidine in position 14, and P14* or ΔP14 describes the deletion of proline in position 14. This nomenclature is known to a person skilled in the field of enzyme technology.

Therefore, the present disclosure also relates to a protease exemplified in that said protease can be obtained from a protease as described above as a starting molecule by single or multiple conservative amino acid substitution, the protease still having at least one of the amino acid substitutions as contemplated herein in the positions that correspond to positions 12, 43, 122, 127, 154, 156, 160, 211, 212, and 222 in SEQ ID NO:1 in the numbering according to SEQ ID NO:1, as described above. The term "conservative amino acid substitution" means the exchange (substitution) of an amino acid residue for another amino acid residue, said exchange not leading to a change in the polarity or charge in the position of the exchanged amino acid, e.g. the exchange of a non-polar amino acid residue for another non-polar amino acid residue. In the context of the present disclosure, conservative amino acid substitutions include, for example: G=A=S, I=V=L=M, D=E, N=Q, K=R, Y=F, S=T, G=A=I=V=L=M=Y=F=W=P=S=T.

Alternatively or additionally, the protease is exemplified in that the protease can be obtained from a protease as contemplated herein as a starting molecule by fragmentation, deletion mutagenesis, insertion mutagenesis, or substitution mutagenesis and comprises an amino acid sequence that matches the starting molecule over a length of at least about 190, about 200, about 210, about 220, about 230, about 240, about 250, about 260, or about 269 interconnected amino acids, the one or more amino acid substitutions contained in the starting molecule still being present in one or more of the positions that correspond to positions 12, 43, 122, 127, 154, 156, 160, 211, 212, and 222 in SEQ ID NO:1.

For example, it is possible to delete individual amino acids at the termini or in the loops of the enzyme without thereby losing or reducing the proteolytic activity. Furthermore, by such fragmentation, deletion mutagenesis, insertion mutagenesis, or substitution mutagenesis, the allergenicity of enzymes in question can also be reduced, for example, and thus the usability of said enzymes can be improved overall. The enzymes advantageously also maintain the proteolytic activity thereof after the mutagenesis, i.e. the proteolytic activity thereof at least corresponds to that of the starting enzyme, i.e. in a preferred embodiment the proteolytic activity is at least about 80%, preferably at least about 90%, of the activity of the starting enzyme. Further substitutions also can exhibit advantageous effects. Both individual amino acids and multiple interconnected amino acids can be exchanged for other amino acids.

Alternatively or in addition, the protease is exemplified in that the protease can be obtained from a protease as contemplated herein as a starting molecule by single or multiple conservative amino acid substitution, the protease having at least one of the amino acid substitutions Q12L, I43V, M122L, D127P, N154S, T156A, G160S, M211N, M211L, P212D, P212H, or A222S in the positions that correspond to positions 12, 43, 122, 127, 154, 156, 160, 211, 212, and 222 according to SEQ ID NO:1.

In further embodiments, the protease is exemplified in that the protease can be obtained from a protease as contemplated herein as a starting molecule by fragmentation, deletion mutagenesis, insertion mutagenesis, or substitution mutagenesis and comprises an amino acid sequence that matches the starting molecule over a length of at least about 190, about 200, about 210, about 220, 230, about 240, about 250, about 260, or about 269 interconnected amino acids, the protease comprising at least one of the amino acid substitutions Q12L, I43V, M122L, D127P, N154S, T156A, G160S, M211N, M211L, P212D, P212H, or A222S in the positions that correspond to positions 12, 43, 122, 127, 154, 156, 160, 211, 212, and 222 according to SEQ ID NO:1.

The further amino acid positions are defined by an alignment of the amino acid sequence of a protease as contemplated herein with the amino acid sequence of the protease from *Bacillus gibsonii* specified in SEQ ID NO:1. Furthermore, the association of the positions is in accordance with the mature protein. This association should also be used in particular when the amino acid sequence of a protease as contemplated herein comprises a greater number of amino acid residues than the protease from *Bacillus gibsonii* according to SEQ ID NO:1. Proceeding from the stated positions in the amino acid sequence of the protease from *Bacillus gibsonii*, the modification positions in a protease as contemplated herein are those that are associated with said positions in an alignment.

Advantageous positions for sequence modifications, in particular substitutions, of the protease from *Bacillus gibsonii* which, transferred to homologous positions of the proteases as contemplated herein, preferably are significant and give the protease advantageous functional properties are accordingly the positions that correspond to positions 12, 43, 122, 127, 154, 156, 160, 211, 212, and 222 in SEQ ID NO:1 in an alignment, i.e. in the numbering according to SEQ ID NO:1. The following amino acid residues are located in the stated positions in the wild-type molecule of the protease from *Bacillus gibsonii*: Q12, I43, M122, D127, N154, T156, G160, M211, P212, and A222.

Further confirmation of the correct association of the amino acids to be modified, i.e. in particular the functional correspondence thereof, can be provided by comparative tests, according to which the two positions associated with each other on the basis of an alignment are modified in the same way in the two proteases compared with each other and it is observed whether the enzymatic activity of the two proteases is changed in the same way. For example, if an amino acid exchange in a certain position of the protease from *Bacillus gibsonii* according to SEQ ID NO:1 is accompanied by a change in an enzymatic parameter, such as an increase in the $K_M$ value, and if a corresponding modification of the enzymatic parameter, e.g. likewise an increase in the $K_M$ value, is observed in a protease variant as contemplated herein, the amino acid exchange of which was achieved by employing the same introduced amino acid, this can be regarded as confirmation of the correct association.

All the mentioned facts are also applicable to the methods as contemplated herein for producing a protease. Accordingly, a method as contemplated herein furthermore comprises one or more of the following method steps:

a) introducing a single or multiple conservative amino acid substitution, the protease comprising at least one of the amino acid substitutions Q12L, I43V, M122L, D127P, N154S, T156A, G160S, M211N, M211L, P212D, P212H, or A222S in the positions that correspond to positions 12, 43, 122, 127, 154, 156, 160, 211, 212, and 222 according to SEQ ID NO:1;

b) modifying the amino acid sequence by fragmentation, deletion mutagenesis, insertion mutagenesis, or substitution mutagenesis in such a way that the protease comprises an amino acid sequence that matches the starting molecule over a length of at least about 190, about 200, about 210, about 220, about 230, about 240, about 250, about 260, or about 269 interconnected amino acids, the protease comprising at least one of the amino acid substitutions Q12L, I43V, M122L, D127P, N154S, T156A, G160S, M211N, M211L, P212D, P212H, or A222S in the positions that correspond to positions 12, 43, 122, 127, 154, 156, 160, 211, 212, and 222 according to SEQ ID NO:1.

All statements also apply to the methods as contemplated herein.

In further embodiments of the present disclosure, the protease, or the protease produced by employing a method as contemplated herein, is still at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, or about 98.8% identical to the amino acid sequence specified in SEQ ID NO:1 over the entire length thereof. Alternatively, the protease, or the protease produced by employing a method as contemplated herein, is still at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, or about 98% identical to one of the amino acid sequences specified in SEQ ID Nos:2-9 over the entire length thereof. The protease, or the protease produced by employing a method as contemplated herein, has an amino acid substitution in at least one of the positions that correspond to positions Q12, I43, M122, D127, N154, T156, G160, M211, P212, or A222, in each case with respect to the numbering according to SEQ ID NO:1. In more preferred embodiments, the amino acid substitution is at least one selected from the group including of Q12L, I43V, M122L, D127P, N154S, T156A, G160S, M211N, M211L, P212D, P212H, and A222S, in each case with respect to the numbering according to SEQ ID NO:1. In other preferred embodiments, the protease comprises one of the following amino acid substitution variants: (I) I43V; (II) M122L, N154S, and T156A; (III) M211N and P212D; (IV) M211L and P212D; (V) G160S; (VI) D127P, M211L, and P212D; (VII) P212H; or (VIII) Q12L, M122L, and A222S, the numbering relating to the numbering according to SEQ ID NO:1 in each case.

The present disclosure also relates to a previously described protease that is additionally stabilized, in particular by employing one or more mutations, such as substitutions, or by coupling to a polymer. As a result of an increase in the stability during storage and/or use, for example during the washing process, the enzymatic activity lasts longer and therefore the cleaning performance is improved. In principle, all stabilization possibilities that are described in the prior art and/or that are advantageous are considered. Stabilizations that are achieved by employing mutations of the enzyme itself are preferred, because such stabilizations do not require any further work steps following the obtainment of the enzyme. Examples of sequence modifications suitable for this purpose are mentioned above. Further suitable sequence modifications are known from the prior art.

Some examples of further possibilities for stabilization are:

modification of the bonding of metal ions, in particular the calcium binding sites, for example by exchanging one or more of the amino acids involved in the calcium binding for one or more negatively charged amino acids and/or by introducing sequence modifications in at least one of the series of the two amino acids arginine/glycine;

protection against the influence of denaturing agents such as surfactants by employing mutations that cause a modification of the amino acid sequence on or at the surface of the protein;

exchange of amino acids located near the N-terminus for amino acids that presumably come into contact with the rest of the molecule by employing non-covalent interactions and thus contribute to the maintenance of the globular structure.

Preferred embodiments are those in which the enzyme is stabilized in several ways, because multiple stabilizing mutations have an additive or synergistic effect.

The present disclosure also relates to a protease as described above that is exemplified in that said protease has at least one chemical modification. A protease having such a modification is called a derivative, i.e. the protease is derivatized.

In the sense of the present application, the term "derivatives" is accordingly understood to mean proteins whose pure amino acid chain has been chemically modified. Such derivatizations can occur in vivo by employing the host cell that expresses the protein, for example. In this regard, couplings of low-molecular-weight compounds, e.g. lipids or oligosaccharides, should be particularly emphasized. Derivatizations can also be performed in vitro, e.g. by employing the chemical conversion of a side chain of an amino acid or by employing covalent bonding of another compound to the protein. For example, amines can be coupled to carboxyl groups of an enzyme in order to change the isoelectric point. Said other compound can also be a further protein, which is bonded to a protein as contemplated herein by employing bifunctional chemical compounds, for example. Derivatization should also be understood to mean covalent bonding to a macromolecular carrier or non-covalent inclusion in suitable macromolecular cage structures. For example, derivatizations can influence the substrate specificity or the strength of bonding to the substrate or cause temporary blocking of the enzymatic activity if the attached substance is an inhibitor. This can be sensible for the storage period, for example. Such modifications can also influence the stability or the enzymatic activity. Such modifications can also be used to reduce the allergenicity and/or immunogenicity of the protein and thus, for example, to increase the skin compatibility of the protein. For example, couplings with macromolecular compounds, such as polyethylene glycol, improve the protein with respect to stability and/or skin compatibility.

In the widest sense, the expression "derivatives of a protein as contemplated herein" can also be understood to mean preparations of said proteins. Depending on the obtainment, processing or preparation, a protein can be combined with various other substances, e.g. from the culture of the producing microorganisms. A protein can also have been mixed with other substances in a specific manner, e.g. in order to increase the storage stability of said protein. Therefore, all preparations of a protein as contemplated herein are also as contemplated herein. This is also independent of whether said protein actually exhibits this enzymatic activity in a certain preparation or not, because it can be desired that said protein has no activity or only slight activity during storage and exhibits the enzymatic function of said protein only at the time of use. This can be controlled by employing appropriate accompanying substances, for example. In particular, the joint preparation of proteases with specific inhibitors is possible in this regard.

Among all proteases and protease variants and/or derivatives described above, those whose catalytic activity at least corresponds to that of the proteases according to SEQ ID Nos: 2-9 and/or whose cleaning performance at least corresponds to that of the proteases according to SEQ ID Nos: 2-9, the cleaning performance being determined in a washing system as described above, are especially preferred in the context of the present disclosure.

The present disclosure also relates to a nucleic acid that codes for a protease as contemplated herein, and to a vector containing such a nucleic acid, in particular a cloning vector or an expression vector.

These can be DNA or RNA molecules. They can exist as a single strand, as a single strand complementary to said single strand, or as a double strand. In particular in the case of DNA molecules, the sequences of both complementary strands in all three possible reading frames must be taken into consideration. Furthermore, it must be considered that different codons, i.e. base triplets, can code for the same amino acids, and therefore several different nucleic acids can code for a certain amino acid sequence. Because of this degeneracy of the genetic code, all nucleic acid sequences that can code for one of the proteases described above are included in this subject matter of the present disclosure. A person skilled in the art is capable of determining these nucleic acid sequences beyond all doubt, because defined amino acids can be associated with individual codons despite the degeneracy of the genetic code. Therefore, on the basis of an amino acid sequence, a person skilled in the art can determine nucleic acids that code for this amino acid sequence without trouble. Furthermore, one or more codons can be replaced by synonymous codons in nucleic acids as contemplated herein. This aspect relates in particular to the heterologous expression of the enzymes as contemplated herein. Every organism, for example a host cell of a production strain, has a certain codon usage. By "codon usage," the translation of the genetic code into amino acids by the particular organism is understood. Bottlenecks can occur in the protein biosynthesis if the codons lying on the nucleic acid are accompanied by a comparatively low number of charged tRNA molecules in the organism. This has the result that a codon is translated less efficiently in the organism than a synonymous codon that codes for the same amino acid, although said codons code for the same amino acid. Because of the presence of a higher number of tRNA molecules for the synonymous codon, the synonymous codon can be translated more efficiently in the organism.

It is possible for a person skilled in the art to produce, on the basis of known DNA sequences and/or amino acid sequences, the corresponding nucleic acids to the point of complete genes by employing methods that are now well known, such as chemical synthesis or polymerase chain reaction (PCR) in conjunction with standard methods of molecular biology and/or protein chemistry. Such methods are known, for example, from Sambrook, J., Fritsch, E. F., and Maniatis, T. 2001. Molecular cloning: a laboratory manual, 3rd Edition Cold Spring Laboratory Press.

In the sense of the present disclosure, the term "vectors" is understood to mean elements that consist of nucleic acids and that contain a nucleic acid as contemplated herein as a characterizing nucleic acid region. Vectors are able to establish said nucleic acid as contemplated herein as a stable genetic element in a species or a cell line over several generations or cells divisions. In particular when used in bacteria, vectors are specific plasmids, i.e. circular genetic elements. In the context of the present disclosure, a nucleic acid as contemplated herein is cloned into a vector. The vectors include, for example, vectors having bacterial plasmids, viruses, or bacteriophages as their origin, or predominantly synthetic vectors or plasmids having elements of widely different origin. By employing the further present genetic elements, vectors are able to establish themselves as stable units in the host cells in question over several generations. They can be present in extrachromosomal form as separate units or can integrate into a chromosome or chromosomal DNA.

Expression vectors comprise nucleic acid sequences that enable them to replicate in the host cells containing them, preferably microorganisms, especially preferably bacteria, and to cause a contained nucleic acid to be expressed there. The expression is influenced in particular by the one or more promoters that regulate the transcription. In principle, the expression can occur by employing the natural promoter originally located before the nucleic acid to be expressed but can also occur by employing a promoter of the host cell provided on the expression vector or by employing a modified promoter or completely different promoter of a different organism or of a different host cell. In the present case, at least one promoter for the expression of a nucleic acid as contemplated herein is provided and is used for the expression of said nucleic acid. Furthermore, expression vectors can be controllable, for example by changing the cultivation conditions or when a certain cell density of the host cells containing the expression vectors is reached or by adding certain substances, in particular activators of the gene expression. An example of such a substance is the galactose derivative isopropyl-β-D-thiogalactopyranoside (IPTG), which is used as an activator of the bacterial lactose operon (lac operon). In contrast to expression vectors, the contained nucleic acid in cloning vectors is not expressed.

The present disclosure also relates to a non-human host cell that contains a nucleic acid as contemplated herein or a vector as contemplated herein or contains a protease as contemplated herein, in particular a non-human host cell that secretes the protease into the medium surrounding the host cell. A nucleic acid as contemplated herein or a vector as contemplated herein is preferably introduced into a microorganism in a transformation process, which microorganism is then a host cell as contemplated herein. Alternatively, individual components, i.e. nucleic acid parts or nucleic acid fragments, of a nucleic acid as contemplated herein can also be introduced into a host cell in such a way that the resulting host cell contains a nucleic acid as contemplated herein or a vector as contemplated herein. This procedure is suitable especially if the host cell already contains one or more components of a nucleic acid as contemplated herein or of a vector as contemplated herein and the further components are then added accordingly. Methods for transforming cells are established in the prior art and are well known to a person skilled in the art. In principle, all cells, i.e. prokaryotic or eukaryotic cells, are suitable as host cells. Host cells that can be advantageously handled genetically, for example with regard to the transformation by employing the nucleic acid or the vector and the stable establishment thereof, are preferred, for example single-cell fungi or bacteria. Furthermore, preferred host cells are distinguished by good microbiological and biotechnological manageability. This relates to, for example, ease of cultivation, high growth rates, low requirements for fermentation media, and good production rates and secretion rates for foreign proteins. Preferred host cells as contemplated herein secrete the (transgenically) expressed protein into the medium surrounding the host cells. Furthermore, the proteases can be modified by the cells that produce the proteases after the production of the proteases, for example by the attachment of sugar molecules, formylations, aminations, etc. Such post-translational modifications can functionally influence the protease.

Additional preferred embodiments are host cells whose activity can be controlled on the basis of genetic regulation elements, which are provided on the vector for example but can also be present in these cells from the outset. Expression of these can be induced, for example, by the controlled addition of chemical compounds that act as activators, by changing the cultivation conditions, or when a certain cell density is reached. This enables economical production of the proteins as contemplated herein. An example of such a compound is IPTG, as described above.

Preferred host cells are prokaryotic or bacterial cells. Bacteria are distinguished by short generation times and low requirements for the cultivation conditions. Thus, economical cultivation methods or production methods can be established. In addition, a person skilled in the art has a wealth of experience at his disposal with regard to bacteria in fermentation technology. For a specific production, gram-negative or gram-positive bacteria can be suitable for a wide range of reasons to be determined experimentally in each individual case, such as nutrient sources, product formation rate, and time requirement.

In the case of gram-negative bacteria such as *Escherichia coli*, a large number of proteins is secreted into the periplasmic space, i.e. into the compartment between the two membranes enclosing the cells. This can be advantageous for specific applications. Furthermore, gram-negative bacteria also can be designed in such a way that they discharge the expressed proteins not only into the periplasmic space but also into the medium surrounding the bacterium. In contrast, gram-positive bacteria, such as Bacilli or actinomycetes or other representatives of the *Actinomycetales* do not have an outer membrane, and therefore secreted proteins are immediately discharged into the medium surrounding the bacteria, generally the nutrient medium, from which the expressed proteins can be purified. Said proteins can be directly isolated from the medium or processed further. In addition, gram-positive bacteria are related or identical to most organisms of origin for technically important enzymes and usually form comparable enzymes themselves, and therefore said bacteria have similar codon usage and the protein synthesis apparatus of said bacteria is of course organized accordingly.

Host cells as contemplated herein can be modified with regard to requirements of said host cells for the culture conditions, can have other or additional selectable markers, or can also express other or additional proteins. In particular, said host cells can also be host cells that transgenically express several proteins or enzymes.

In principle, the present disclosure can be applied to all microorganisms, in particular to all microorganisms capable of fermentation, especially preferably to those of the genus *Bacillus*, and has the result that proteins as contemplated herein can be produced by using such microorganisms. Such microorganisms are then host cells as contemplated herein.

In a further embodiment of the present disclosure, the host cell is exemplified in that said host cell is a bacterium, preferably a bacterium selected from the group of genera comprising *Escherichia, Klebsiella, Bacillus, Staphylococcus, Corynebacterium, Arthrobacter, Streptomyces, Stenotrophomonas*, and *Pseudomonas*, more preferably a bacterium selected from the group comprising *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor*, and *Stenotrophomonas maltophilia*.

However, the host cell can also be a eukaryotic cell, which has a nucleus. Therefore, the present disclosure also relates to a host cell that is exemplified in that said host cell has a nucleus. In contrast to prokaryotic cells, eukaryotic cells are capable of post-translationally modifying the formed protein. Examples are fungi such as actinomycetes or yeasts such as *Saccharomyces* or *Kluyveromyces*. This can be especially advantageous when, for example, the proteins should experience, in conjunction with their synthesis, specific modifications that such systems enable. The modifications that eukaryotic systems perform especially in conjunction with the protein synthesis include, for example, the binding of low-molecular-weight compounds such as membrane anchors or oligosaccharides. Such oligosaccharide modifications can be desirable in order to reduce the allergenicity of an expressed protein, for example. Coexpression with the enzymes naturally formed by such cells, such as cellulases, can also be advantageous. Furthermore, thermophilic-fungus expressions systems, for example, are especially suitable for the expression of temperature-resistant proteins or variants.

The host cells as contemplated herein are cultivated and fermented in a typical manner, for example in discontinuous or continuous systems. In the first case, a suitable nutrient medium is inoculated with the host cells and the product is harvested from the medium after a time period to be determined experimentally. Continuous fermentations are distinguished by the attainment of a steady state in which, over a comparatively long time period, some cells die off but new cells are also grown and at the same time the formed protein can be retrieved from the medium.

Host cells as contemplated herein are preferably used to produce proteases as contemplated herein. Therefore, the present disclosure also relates to a method for producing a protease, comprising
a) cultivating a host cell as contemplated herein, and
b) isolating the protease from the culture medium or from the host cell.

This subject matter of the present disclosure preferably comprises fermentation methods. Fermentation methods are known per se from the prior art and are the actual large-scale production step, generally followed by a suitable method for purifying the produced product, for example the proteases as contemplated herein. All fermentation methods based on a corresponding method for producing a protease as contemplated herein are embodiments of this subject matter of the present disclosure.

In particular, fermentation methods that are exemplified in that the fermentation is performed by employing a supply strategy are considered. In this case, the medium constituents that are consumed by the continuous cultivation are added. Considerable increases both in the cell density and in the cell mass or dry mass and/or in particular in the activity of the protease of interest can thereby be achieved. Furthermore, the fermentation can also be designed in such a way that undesirable metabolic products are filtered out or are neutralized by the addition of buffer or suitable counterions.

The produced protease can be harvested from the fermentation medium. Such a fermentation method is preferred over isolation of the protease from the host cell, i.e. over product processing from the cell mass (dry mass), but requires that suitable host cells or one or more suitable secretion markers or secretion mechanisms and/or transport systems are provided so that the host cells secrete the protease into the fermentation medium. Without secretion, the protease can alternatively be isolated from the host cell, i.e. can be purified from the cell mass, for example by precipitation with ammonium sulfate or ethanol or by chromatographic purification.

All the facts presented above can be combined into methods in order to produce a protease as contemplated herein.

The present disclosure also relates to an agent that is exemplified in that the agent contains a protease as contemplated herein as described above. The agent is preferably a washing or cleaning agent.

This subject matter of the present disclosure includes all conceivable types of washing or cleaning agent, both concentrates and agents to be used undiluted, for use on a commercial scale, in a washing machine, or in washing or cleaning by hand. Included are, for example, washing agents for textiles, carpets, or natural fibers, for which the designation "washing agent" is used. Also included are, for example, dishwashing agents for dishwashers (automatic dishwashing agents) or manual dishwashing agents or cleaners for hard surfaces such as metal, glass, porcelain, ceramic, tiles, stone, painted surfaces, plastics, wood, or leather, for which the designation "cleaning agent" is used, i.e. in addition to manual dishwashing agents and automatic dishwashing agents, also scouring agents, glass cleaners, and fragrant toilet rim blocks, for example. The washing and cleaning agents in the context of the present disclosure also include washing additives, which are added to the actual washing agent in the washing of textiles manually or by machine in order to achieve further action. Furthermore, washing and cleaning agents in the context of the present disclosure also include textile pretreatment and posttreatment agents, i.e. agents with which the laundry item is brought into contact before the actual washing, for example in order to loosen tenacious soiling, and agents that give the items to be washed further desirable properties, such as pleasant texture, freedom from wrinkles, or low static charge, in a step following the actual textile washing. The softeners, inter alia, are included among the agents mentioned last.

The dishwashing agent as contemplated herein can be an automatic dishwashing agent or a manual dishwashing agent. Automatic dishwashing agents are cleaning agents optimized for use in dishwashers. Automatic dishwashing agents are preferably in solid form. Manual dishwashing agents are optimized for hand washing. Manual dishwashing agents are preferably liquid. The agents as contemplated herein are preferably automatic dishwashing agents.

The washing or cleaning agents as contemplated herein, which can be in the form of powdery solids, subsequently compacted particles, or homogeneous solutions or suspensions, can contain all known ingredients common in such agents in addition to a protease as contemplated herein, at least one further ingredient preferably being present in the agent. The agents as contemplated herein can contain, in particular, surfactants, builders, peroxygen compounds, or bleach activators. Furthermore, the agents as contemplated herein can contain water-miscible organic solvents, further enzymes, sequestering agents, electrolytes, pH regulators, and/or further auxiliaries such as optical brighteners, graying inhibitors, foam regulators, dyes, and fragrances, and combinations thereof.

In particular, a combination of a protease as contemplated herein with one or more further ingredients of the agent is advantageous, because in preferred embodiments as contemplated herein such an agent has improved cleaning performance because of resulting synergies. In particular, such a synergy can be achieved by the combination of a protease as contemplated herein with a surfactant and/or a builder and/or a peroxygen compound and/or a bleach activator. However, in preferred embodiments, the agent as contemplated herein cannot contain boric acid.

Advantageous ingredients of agents as contemplated herein are disclosed in international patent application WO 2009/121725 from page 5, next to last paragraph to page 13, after the second paragraph. Reference is expressly made to this disclosure, and the disclosure content there is incorporated into the present patent application.

An agent as contemplated herein contains the protease advantageously in an amount of from about 2 µg to about 20 mg, preferably from about 5 µg to about 17.5 mg, especially preferably from about 20 µg to about 15 mg, and exceedingly preferably from about 50 µg to about 10 mg per gram of the agent. Furthermore, the protease contained in the agent and/or further ingredients of the agent can be encased in a substance that is impermeable to the enzyme at room temperature or in the absence of water and that is permeable to the enzyme under conditions of use of the agent. Such an embodiment of the present disclosure is therefore exemplified in that the protease is encased in a substance that is impermeable to the enzyme at room temperature or in the absence of water. Furthermore, the washing or cleaning agent itself can also be packaged in a container, preferably an air-permeable container, from which the washing or cleaning agent is released shortly before use or during the washing/dishwashing process.

Said embodiments of the present disclosure comprise all solid, powdery, liquid, gel, or pasty product forms of agents as contemplated herein, which optionally can also consist of multiple phases and can exist in compressed or uncompressed form. The agent can exist as a free-flowing powder, in particular with an apparent density of from about 300 g/l to about 1200 g/l, in particular from about 500 g/l to about 900 g/l or from about 600 g/l to about 850 g/l. The solid product forms of the agent also include extrudates, granulates, tablets, and pouches. Alternatively, the agent can also be liquid, gel, or pasty, e.g. in the form of a non-aqueous agent or a non-aqueous paste or in the form of an aqueous agent or a water-containing paste. Furthermore, the agent can exist as a single-component system. Such agents consist of one phase. Alternatively, an agent can also consist of multiple phases. Such an agent is accordingly divided into multiple components. Preferred product forms are solid forms, such as single-phase or multiphase tablets ("tabs") or low-water to water-free liquids/gels, both preferably in unit dosage form.

Washing or cleaning agents as contemplated herein can contain only one protease. Alternatively, said washing or cleaning agents can also contain further hydrolytic enzymes or other enzymes at a concentration that is advantageous for the effectiveness of the agent. A further embodiment of the present disclosure therefore relates to agents that also comprise one or more further enzymes. Preferably usable as further enzymes are all enzymes that can exhibit catalytic activity in the agent as contemplated herein, in particular a lipase, amylase, cellulase, hemicellulase, mannanase, tannase, xylanase, xanthanase, xyloglucanase, β-glucosidase, pectinase, carrageenase, perhydrolase, oxidase, oxidoreductase, or other protease distinguishable from the protease as contemplated herein, and mixtures thereof. Further enzymes are each advantageously contained in the agent in an amount of from about $1 \times 10^{-8}$ to about 5 wt. % in relation to active protein. More preferably, every further enzyme is contained in agents as contemplated herein in an amount of from about $1 \times 10^{-7}$ to about 3 wt. %, from about 0.00001 to about 1 wt. %, from about 0.00005 to about 0.5 wt. %, from about 0.0001 to about 0.1 wt. %, and especially preferably from about 0.0001 to about 0.05 wt. %, in relation to active protein. The enzymes especially preferably exhibit synergistic cleaning performance with respect to certain stains or spots, i.e. the enzymes contained in the agent composition support each other in the cleaning performance of said enzymes. Such a synergy exceedingly preferably exists between the protease contained as contemplated herein and a further enzyme of an agent as contemplated herein, including in particular between said protease and an amylase and/or a lipase and/or a mannanase and/or a cellulase and/or a pectinase. Synergistic effects can occur not only between different enzymes but also between one or more enzymes and further ingredients of the agent as contemplated herein.

In the cleaning agents described herein, the enzymes to be used can also be prepared together with accompanying substances, e.g. from the fermentation. In liquid formulations, the enzymes are preferably used as enzyme liquid formulation(s).

The enzymes are generally provided not in the form of the pure protein but rather in the form of stabilized, storable and transportable preparations. These pre-prepared preparations include, for example, the solid preparations obtained by granulation, extrusion, or lyophilization or, in particular in the case of liquid or gel agents, solutions of the enzymes, advantageously as concentrated as possible, with little water, and/or mixed with stabilizers or further auxiliary agents.

Alternatively, both for the solid product form and the liquid product form, the enzymes can be encapsulated, e.g. by spray drying or extrusion of the enzyme solution together with a preferably natural polymer or in the form of capsules, e.g. those in the case of which the enzymes are encapsulated as in a solidified gel, or in those of the core-shell type, in the case of which an enzyme-containing core is coated with a water-, air-, and/or chemical-impermeable protective layer. In overlaid layers, further active ingredients, such as stabilizers, emulsifiers, pigments, bleaching agents, or dyes, can be additionally applied. Such capsules are applied using methods that are known per se, for example by shaking granulation or roll granulation or in fluidized bed processes. Such granulates are advantageously low in dust, for example due to the application of polymeric film formers, and stable in storage due to the coating.

The enzymes can also be introduced into water-soluble films. Such a film enables the release of the enzymes after contact with water. As used here, the term "water-soluble" refers to a film structure that is preferably completely water-soluble. However, films that are substantially water-soluble but have relatively small amounts of a water-insoluble material in the film structure, films having materials that are water-soluble only at relatively high water temperatures or only under restricted pH conditions, and films that include a relatively thin layer of water-insoluble material are all also included in the term "water-soluble." Such a film preferably of (completely or partially hydrolyzed) polyvinyl alcohol (PVA). The film can also contain, exclusively or in addition to the PVA, acid/acrylate copolymers, preferably methacrylic acid/ethyl acrylate copolymer, such as that available from Beiland as GBC 2580 and 2600, sytrene/maleic anhydride copolymer (SMA) (available as Scripset (brand name) from Monsanto), ethylene/acrylic acid copolymer (EAA) or metal-salt-neutralized ethylene/methacrylic acid copolymer (EMAA), known as an ionomer (available from DuPont), the acid content of EAA or EMAA being at least approximately 20 mol %, polyether block amide copolymer, polyhydroxyvaleric acid (available as Biopol (brand name) resins from Imperial Chemical Industries), polyethylene oxide, water-soluble polyester or copolyester, polyethyloxazoline (PEOX 200 from Dow), and water-soluble polyurethane.

Moreover, it is possible to prepare two or more enzymes together, so that a single granulate has several enzyme activities.

The present disclosure also relates to a method for cleaning textiles or hard surfaces, which is exemplified in that an agent as contemplated herein is used in at least one method step or that a protease as contemplated herein becomes catalytically active in at least one method step, in particular such that the protease is used in an amount of from about 40 µg to about 4 g, preferably from about 50 µg to about 3 g, especially preferably from about 100 µg to about 2 g, and exceedingly preferably from about 200 µg to about 1 g.

In various embodiments, the method described above is distinguished in that the protease is used at a temperature of from 0 to about 100° C., preferably from about 10 to about 70° C., more preferably from about 30 to about 50° C., and most preferably about 45° C.

This includes both manual methods and methods by machine, methods by machine being preferred. In general, methods for cleaning textiles are distinguished in that, in several method steps, various substances that are active in cleaning are applied to the goods to be cleaned and are washed off after the exposure time, or that the goods to be cleaned are treated in some other way with a washing agent or a solution or dilution of said agent. The same applies, *mutatis mutandis*, to methods for cleaning all other material than textiles, in particular hard surfaces. All conceivable washing or cleaning methods can be enriched with the use of a washing or cleaning agent as contemplated herein or a protease as contemplated herein in at least one of the method steps and are then embodiments of the present disclosure. All facts, subject matter, and embodiments that are described for a protease as contemplated herein and agents containing said protease are also applicable to this subject matter of the present disclosure. Therefore, reference is expressly made here to the disclosure at the corresponding location, this disclosure also applying to the aforementioned methods as contemplated herein.

In general, agents described herein, in particular dishwashing agents, can be prepared in different ways. The agents can be in solid or liquid product formats or can exist as a combination of solid and liquid product formats. In particular, powders, granulates, extrudates, and compacted products, in particular tablets, are suitable as solid product formats. The liquid product formats based on water and/or organic solvents can be in a thickened state, in the form of gels. The agents can be prepared in the form of multiphase products. The individual phases of such multiphase agents can have the same state of matter or different states of matter.

The agents, in particular dishwashing agents, can exist as shaped bodies. In order to facilitate the breakdown of such prefabricated shaped bodies, it is possible to incorporate disintegration auxiliaries, i.e. tablet disintegrants, into said agents in order to shorten the breakdown times. The terms "tablet disintegrants" and "breakdown accelerators" are understood to mean auxiliaries that provide for the quick breakdown of tablets in water or other media and for the rapid release of the active ingredients. Preferably, disintegration auxiliaries can be used in amounts of from about 0.5 to about 10 wt. %, preferably from about 3 to about 7 wt. %, and in particular from about 4 to about 6 wt. %, in relation to the total weight of the disintegration-auxiliary-containing agent.

The agents, in particular dishwashing agents, more preferably automatic dishwashing agents, described herein are preferably prefabricated as dosage units. Said dosage units preferably comprise the amount of substances active in cleaning that is necessary for one cleaning operation. Preferred dosage units have a weight of between from about 12 and about 30 g, preferably between from about 14 and about 26 g, and in particular between from about 15 and about 22 g. The volume of the aforementioned dosage units and the spatial shape thereof are especially preferably selected in such a way that it is ensured that the prefabricated units can be dosed by employing the dosing chamber of a dishwasher. The volume of the dosing unit is therefore preferably between from about 10 and about 35 ml, preferably between from about 12 and about 30 ml.

The agents, in particular dishwashing agents, in particular the prefabricated dosing units, especially preferably have a water-soluble wrapping.

The water-soluble wrapping is preferably formed from a water-soluble film material, which is selected from the group of polymers and polymer mixtures. The wrapping can be formed from one or from two or more layers of the water-soluble film material. The water-soluble film material of the first layer and of the further layers, if present, can be the same or different. Especially preferred are films which, for example, can be adhesively bonded and/or sealed to form packagings such as tubes or cushions after said films have been filled with an agent.

The water-soluble packaging can have one or more chambers. The agent can be contained in one or more chambers, if present, of the water-soluble wrapping. The amount of agent preferably corresponds to the full dose or half of the dose that is required for a washing cycle.

It is preferred that the water-soluble wrapping contains polyvinyl alcohol or a polyvinyl alcohol copolymer. Water-soluble wrappings that contain polyvinyl alcohol or a polyvinyl alcohol copolymer have good stability together with sufficiently high water solubility, in particular cold-water solubility.

Suitable water-soluble films for producing the water-soluble wrapping are preferably based on a polyvinyl alcohol or a polyvinyl alcohol copolymer having a molecular weight in the range of from about 5,000 to about 1,000,000 g/mol, preferably from about 20,000 to about 500,000 g/mol, especially preferably from about 30,000 to about 100,000 g/mol, and in particular from about 40,000 to about 80,000 g/mol.

Polyvinyl alcohol is typically produced by hydrolyzing polyvinyl acetate, because the direct synthesis pathway is not possible. The case is similar for polyvinyl alcohol copolymers, which are produced accordingly from polyvinyl acetate copolymers. It is preferred if at least one layer of the water-soluble wrapping comprises a polyvinyl alcohol whose degree of hydrolysis makes up from about 70 to about 100 mol %, preferably from about 80 to about 90 mol %, especially preferably from about 81 to about 89 mol %, and in particular from about 82 to about 88 mol %.

A polymer selected from the group comprising (co) polymers containing (meth)acrylic acid, polyacrylamides, oxazoline polymers, polystyrene sulfonates, polyurethanes, polyesters, polyethers, polylactic acid, or mixtures of the aforementioned polymers can additionally be added to a polyvinyl-alcohol-containing film material suitable for producing the water-soluble wrapping. Polylactic acids are preferred additional polymers.

Preferred polyvinyl alcohol copolymers comprise dicarboxylic acids as further monomers in addition to vinyl alcohol. Suitable dicarboxylic acids are itaconic acid, malonic acid, succinic acid, and mixtures thereof, itaconic acid being preferred.

Likewise, preferred polyvinyl alcohol copolymers comprise an ethylenically unsaturated carboxylic acid or a salt or ester thereof in addition to vinyl alcohol. Such polyvinyl alcohol copolymers especially preferably contain acrylic acid, methacrylic acid, acrylic acid ester, methacrylic acid ester, or mixtures thereof in addition to vinyl alcohol.

It can be preferred that the film material contains further additives. The film material can contain, for example, plasticizers such as dipropylene glycol, ethylene glycol, diethylene glycol, propylene glycol, glycerol, sorbitol, mannitol, or mixtures thereof. Further additives include, for example, release aids, fillers, cross-linking agents, surfactants, antioxidants, UV absorbers, anti-blocking agents, anti-sticking agents, or mixtures thereof.

Films sold by the company MonoSol LLC, for example under the designation M8630, C8400, or M8900, are suitable water-soluble films for use in the water-soluble wrappings of the water-soluble packagings as contemplated herein. Other suitable films include films with the name Solublon® PT, Solublon® GA, Solublon® KC, or Solublon® KL from Aicello Chemical Europe GmbH or the films VF-HP from Kuraray.

According to a preferred embodiment, the agent, in particular dishwashing agent, is tightly wrapped in a water-soluble film.

The water-soluble film that is preferably used in the tight wrapping especially preferably comprises polyvinyl alcohol, as described above, a thickness of from about 10 μm to about 100 μm, in particular from about 12 μm to about 60 μm, especially preferably from about 15 μm to about 50 μm, especially from about 20 μm to about 40 μm, in particular from about 22 μm to about 35 μm, being used as an starting thickness.

In the case of a tight wrapping, a single-use portion of the cleaning agent is wrapped. For the wrapped cleaning agent single-use portion as contemplated herein, it is important that the wrapping lies tightly against the surface of the tablets at every point of the tablets. Ideally, the wrapping is even under stress, but this is not absolutely required. This tight contact of the wrapping is favorable for the breakdown: Upon first contact with water, the wrapping will let a small amount of water through in some location. The wrapping does not have to dissolve at all at first. In this location, the disintegrant contained in the tablet begins to swell. As a result, the wrapping then tears open suddenly because of the volume increase of the tablet and releases the tablet. If the wrapping is not in tight contact, the mechanism described here does not function, because the tablet can swell without thereby bursting the wrapping. The use of a swellable disintegration agent is superior to a gas-developing system, because the bursting effect of said disintegration agent always leads to the tearing open of the wrapping. In the case of a gas-developing system, the bursting effect can "fizzle out" as a result of the gas escaping from a leak.

Preferred cleaning agent single-use portions as contemplated herein are exemplified in that the distance between the single-use portion and the water-soluble wrapping is from about 0.1 to about 1000 μm, preferably from about 0.5 to about 500 μm, especially preferably from about 1 to about 250 μm, and in particular from about 2.5 to about 100 μm, over the entire area.

In a preferred embodiment, the film wrapping is initially loosely laid around a cleaning agent single-use portion and welded and then is shrunk onto said cleaning agent single-use portion so that there is tight contact between the film packaging and the cleaning agent concentrate. Accordingly, cleaning agent single-use portions as contemplated herein are exemplified in that the wrapping is a film packaging shrunk onto said cleaning agent single-use portions.

For example, this wrapping can be achieved by laying a water-soluble base film onto a transport chain or a shaping tool, then placing one or more washing or cleaning agent portions onto the base film, subsequently laying a water-soluble top film onto the cleaning agent portion(s) on the base film, and then fastening the top film to the base film, the cleaning agent portion(s) thus being enclosed.

Alternatively, this step can also be performed using a single-stranded film, which is then laid around the single-use portions as a tube. Then the films are sealed and optionally cut. Then the film can be shrunk on by employing hot air or infrared radiation, optionally with pressing.

Such water-soluble wrappings are also already described in patent applications WO 2004/031338 A and WO 2003/099985 A, to the entire disclosure of which reference is hereby made.

The present disclosure also relates to the corresponding use of the dishwashing agents as contemplated herein. The present disclosure also relates to a dishwashing method, in particular a dishwashing method by machine or a manual dishwashing method, wherein a dishwashing agent as contemplated herein is used. Therefore, the present application also relates to a method for cleaning dishes, wherein the agent as contemplated herein is used. If the dishwashing agent as contemplated herein is an automatic dishwashing agent, the agent can be dosed into the interior of a dishwasher while a dishwashing program is running, before the main washing cycle begins or during the main washing cycle. The dosing or introducing of the agent as contemplated herein into the interior of the dishwasher can be performed manually, but the agent is preferably dosed into the interior of the dishwasher by employing the dosing chamber.

Because proteases as contemplated herein naturally already have hydrolytic activity and also exhibit this hydrolytic activity in media that otherwise have no cleaning power, such as in mere buffer, a single step and/or the only step of such a method can consist in the bringing of a protease as contemplated herein into contact with the stain as the only component active in cleaning, preferably in a buffer solution or in water. This is a further embodiment of this subject matter of the present disclosure.

Further alternative embodiments of this subject matter of the present disclosure are methods for treating textile raw materials or for textile care, wherein a protease as contemplated herein becomes active in at least one method step. Among these, methods for textile raw materials, fibers, or textiles having natural components are preferred, especially methods for those with wool or silk.

Finally, the present disclosure also relates to the use of the proteases described herein in washing or cleaning agents, e.g. as described above, for the (improved) removal of protein-containing stains, e.g. on textiles or hard surfaces.

All facts, subject matter, and embodiments that are described for a protease as contemplated herein and agents containing said protease are also applicable to this subject matter of the present disclosure. Therefore, reference is expressly made here to the disclosure at the corresponding location, this disclosure also applying to the aforementioned use as contemplated herein.

EXAMPLES

Overview of the Mutations of the Variants:

| Variant | Sequence | | | SEQ ID NO: |
|---|---|---|---|---|
| Mutant 1 | I43V | | | 2 |
| Mutant 2 | M122L | N154S | T156A | 3 |
| Mutant 3 | M211N | P212D | | 4 |
| Mutant 4 | M211L | P212D | | 5 |
| Mutant 5 | G160S | | | 6 |
| Mutant 6 | D127P | M211L | P212D | 7 |
| Mutant 7 | P212H | | | 8 |
| Mutant 8 | Q12L | M122L | A222S | 9 |

Determining the Activity of the Protease

The protease activity is determined in a discontinuous assay, in which casein is used as a substrate. The final concentration of the substrate solution is 12 mg/ml casein (produced according to Hammarsten; Merck, Darmstadt, #2242) and 30 mM tris in synthetic tap water. Synthetic tap water is a solution of 0.029% (w/v) $CaCl_2 \cdot 2H_2O$, 0.014% (w/v) $MgCl_2 \cdot 6H_2O$, and 0.021% (w/v) $NaHCO_3$ having 15° dH (German hardness). The substrate solution is heated to 70° C. and the pH thereof is set to 8.5 at 50° C. by using 0.1 N NaOH. The protease solution is produced by adding 2%

(w/v) water-free pentasodium tripolyphosphate to synthetic tap water and setting the pH to 8.5 by employing hydrochloric acid. 200 µl of the enzyme solution is added to 600 µl of the casein solution. The mixture is incubated at 50° C. for 15 minutes. The reaction is ended by adding 600 µl of 0.44 M trichloroacetic acid (TCA), 0.22 M sodium acetate in 3% (w/v). After a cooling step of 15 minutes on ice, the TCA-insoluble protein is removed by centrifugation. 900 µl of the remaining solution is mixed with 300 µl of 2 N NaOH, and the absorption of this mixture, which contains TCA-soluble proteins, is measured at 290 µm. Control values are produced by adding 600 µl of TCA solution to 600 µl of casein solution and then adding 200 µl of enzyme solution. A protease solution that causes an absorption change of 0.500 OD at 290 nm under these conditions has an activity of 10 HPE per ml according to the present notation.

Examination of the Variants in a Dishwashing Agent Matrix

A phosphate-free commercially available automatic dishwashing agent in the form of a dishwashing agent tablet. The tablet weight was 19 g. The dishwashing agent matrix had the following composition:

| Raw material | P-free formula ranges Total | |
|---|---|---|
| | % | g/job |
| Sodium citrate | 15.00-20.00 | 3.00-4.00 |
| Phosphonate (HEDP) | 2.50-7.50 | 0.50-1.50 |
| MG DA | 0.00-25.00 | 0.00-1.50 |
| Sodium disilicate | 5.00-35.00 | 1.00-7.00 |
| Soda | 12.50-25.00 | 2.50-5.00 |
| Sodium percarbonate | 10.00-15.00 | 2.00-3.00 |
| Bleach catalyst (Mn-based) | 0.02-0.50 | 0.003-0.10 |
| TAED | 2.00-3.00 | 0.40-0.60 |
| Non-ionic surfactant, 20-40 EO, end-cap | 2.50-10.00 | 0.50-2.00 |
| Polycarboxylate | 5.00-10.00 | 1.00-2.00 |
| Cationic copolymer | 0.25-0.75 | 0.05-0.15 |
| Cross-linked PVP | 0.00-1.50 | 0.00-0.30 |
| Protease | 1.50-5.00 | 0.30-1.00 |
| Amylase | 0.50-3.00 | 0.10-0.60 |
| Benzotriazole (silver protection) | 0.00-0.50 | 0.00-0.10 |
| Perfume | 0.05-0.15 | 0.01-0.03 |
| Dye solution | 0.00-1.00 | 0.00-0.20 |
| Zinc acetate | 0.10-0.30 | 0.02-0.06 |
| Sodium sulfate | 0.00-25.00 | 0.00-5.00 |
| Water | 0.00-1.50 | 0.00-0.30 |
| pH adjuster (citric acid) | 1.00-1.50 | 0.20-0.30 |
| Process agent | 0.00-5.00 | 0.00-1.00 |
| | 57.92-196.20 | 11.6-39.24 | calculated on the basis of a 20-g tablet (the tablet can also weigh 17 to 20 g)

The cleaning performance describes the ability of a dishwashing agent, in particular an automatic dishwashing agent, to partially or completely remove a stain that is present. The cleaning performance of the agent was tested on various stubborn stains. The protease variants as contemplated herein were separately added to the agent used.

The dishwashing method was performed in the Miele GSL dishwasher (program: 45° C., holding time of 8 minutes, program duration of 57 minutes, water hardness of 21° German hardness) in accordance with IKW standard.

The dishwashing agent tablet was placed in the dosing device before the start of the cleaning program.

The cleaning performance was evaluated visually in accordance with a scale from 1 to 10, the value 10 representing the best cleaning performance (no detectable residue). Three repetitions with six internal replications each per machine are performed. The indicated results are the mean of the multiple determination.

The following delta values in comparison with the wild-type protease (SEQ ID NO:1) resulted:

| | Tea (Assam) | Tea (BOP) | Ground meat | Spaghetti | Crème brûlée |
|---|---|---|---|---|---|
| Variant 1 | no data | no data | 1.4 | 1.1 | 0.4 |
| Variant 2 | 0.8 | 0.8 | 1.6 | 0.6 | no data |
| Variant 3 | 0.6 | 0.6 | 0.6 | 1.2 | 0.4 |
| Variant 4 | 1.0 | 0.9 | 0.9 | 1.1 | 1.2 |
| Variant 5 | 0.7 | 0.1 | 0.7 | 1.3 | no data |
| Variant 6 | 1.2 | 0.7 | no data | 0.9 | no data |
| Variant 7 | no data | no data | no data | 1.0 | no data |
| Variant 8 | 0.6 | 1.0 | no data | no data | no data |

As can be seen, the use of the protease variants leads to an improvement in the cleaning performance. In particular, variants 4, 6, and 8 lead to an improvement on tea stains. Variants 1 and 2 show particular advantages on ground meat and variants 1, 3, 4, 5, and 7 on spaghetti. Furthermore, in the case of variant 4, a particular advantage on crème brûlée can be observed.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A protease having protease activity and having an amino acid sequence that has at least 82% sequence identity to the amino acid sequence specified in SEQ ID NO:1 over the entire length thereof and that has an amino acid substitutions in at least the positions that correspond to positions M211L and P212D with respect to the numbering according to SEQ ID NO:1.

2. The protease according to claim 1, wherein the protease has at least one amino acid substitution being selected from the group of Q12L, I43V, D127P, N154S, T156A, G160S, and A222S, in each case with respect to the numbering according to SEQ ID NO:1.

3. The protease according to claim 1, wherein the protease has at least one of the following amino acid substitutions, in each case with respect to the numbering according to SEQ ID NO:1:
 (i) I43V;
 (ii) M122L, N154S, and T156A;
 (iii) G160S;
 (iv) D127P;
 (v) P212H; or
 (vi) Q12L, M122L, and A222S.

4. An agent, wherein the agent comprises at least one protease according to claim 1.

5. The agent according to claim 4, wherein the agent is a dishwashing agent.

6. The protease of claim 1, wherein the protease has utility in a washing or cleaning agent to remove peptide- or protein-containing stains.

7. The agent according to claim 5, wherein the dishwashing agent is further defined as an automatic dishwashing agent.

8. The protease of claim 1, wherein the protease comprises an amino acid substitution in a position that corresponds to position I43V with respect to the numbering according to SEQ ID NO: 1.

9. The protease of claim 1, wherein the protease comprises amino acid substitutions in positions that correspond to positions M122L, N154S, and T156A with respect to the numbering according to SEQ ID NO: 1.

10. The protease of claim 1, wherein the protease comprises an amino acid substitution in a position that corresponds to position G160S with respect to the numbering according to SEQ ID NO:1.

11. The protease of claim 1, wherein the protease comprises an amino acid substitution in a position that corresponds to position D127P with respect to the numbering according to SEQ ID NO:1.

12. The protease of claim 1, wherein the protease comprises an amino acid substitution in a position that corresponds to position P212H with respect to the numbering according to SEQ ID NO:1.

13. The protease of claim 1, wherein the protease comprises amino acid substitutions in positions that correspond to positions Q12L, M122L, and A222S with respect to the numbering according to SEQ ID NO:1.

14. The protease of claim 1, wherein the protease has an amino acid sequence that has at least 94% sequence identity to the amino acid sequence specified in SEQ ID NO:1 over the entire length thereof.

* * * * *